United States Patent [19]

Monnais et al.

[11] Patent Number: 4,511,360
[45] Date of Patent: Apr. 16, 1985

[54] DYEING COMPOSITIONS BASED ON OXIDATION DYESTUFF PRECURSORS AND ON NITRO BENZENE DYESTUFFS AND THEIR USE FOR DYEING KERATIN FIBRES

[75] Inventors: Christian Monnais, Neuilly-sur-Seine; Jean Cotteret, Franconville; Andreè Bugaut, Boulogne-Billancourt, all of France

[73] Assignee: L'Oreal, Paris, France

[21] Appl. No.: 311,309

[22] Filed: Oct. 14, 1981

[30] Foreign Application Priority Data

Oct. 16, 1980 [LU] Luxembourg ............... 82860

[51] Int. Cl.³ .................................................. A61K 7/13
[52] U.S. Cl. ............................................. 8/405; 8/406; 8/407; 8/408; 8/414; 8/415; 8/428
[58] Field of Search ............... 8/406, 408, 414, 415, 8/405, 407, 428

[56] References Cited

U.S. PATENT DOCUMENTS 3,591,638  7/1971  Halasz ................................. 8/415
3,973,900  8/1976  Husemeyer et al. .
4,361,421  11/1982  Bugaut et al. ..................... 8/410

FOREIGN PATENT DOCUMENTS 2830497  7/1978  Fed. Rep. of Germany .
1403928  8/1975  United Kingdom .
1520787  8/1978  United Kingdom .
1531605  11/1978  United Kingdom .
1549752  8/1979  United Kingdom .
2066860  7/1981  United Kingdom .

OTHER PUBLICATIONS

Ames et al., "Hair Dyes Are Mutagenic: Identification of a Variety of Mutagenic Ingredients", *Proc. Nat. Acad. Sci.*, vol. 72, No. 6, pp. 2423–2427, Jun. 1975.
Ames et al., "Methods for Detecting Carcinogens and Mutagens with Salmonella Mammalian Microsome Mutagenicity Test", *Mutation Res.*, 31, (1975), pp. 347–364.
Chemical Abstracts, vol. 53, 11343g, (Chem. Ber. 92, 407–414), 1959.
Chemical Abstracts, vol. 22, No. 8, Apr. 2, 1928, p. 1352, paragraph 4.
Chemical Abstracts, vol. 84, No. 19, Mar. 10, 1976, p. 502, 135665a.
Chemical Abstracts, vol. 54, 17317d, (Monatsch. Chem. 90, 683–687), 1959.
The Merck Index, 9th ed., 1976.

*Primary Examiner*—Albert T. Meyers
*Assistant Examiner*—John M. Kilcoyne
*Attorney, Agent, or Firm*—Fleit, Jacobson, Cohn & Price

[57] ABSTRACT

Dyeing compositions are disclosed which comprise at least one oxidation dyestuff precursor in combination with at least one direct dyestuff, in an aqueous vehicle, the direct dyestuff being a nitro derivative of the benzene series having the formula:

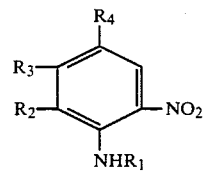

in which $R_1$ denotes the methyl group, $R_2$ and $R_4$ denote hydrogen and $R_3$ denotes the β-hydroxyethoxy group, or alternatively $R_1$, $R_3$ and $R_4$ denote hydrogen and $R_2$ denotes the methyl or hydroxyl group, or alternatively $R_1$ and $R_2$ denote hydrogen, $R_3$ denotes the methyl group and $R_4$ denotes the hydroxyl, (β-hydroxyethyl)-amino or (β-N,N-diethylaminoethyl)-amino group, or $R_1$, $R_2$ and $R_3$ denote hydrogen and $R_4$ denotes the N,N-bis-(β-hydroxyethyl)-amino group.

21 Claims, No Drawings

DYEING COMPOSITIONS BASED ON OXIDATION DYESTUFF PRECURSORS AND ON NITRO BENZENE DYESTUFFS AND THEIR USE FOR DYEING KERATIN FIBRES

The present invention relates to dyeing compositions comprising a combination of oxidation dyestuff precursors and nitro direct dyestuffs of the benzene series, which have the property of being stable in a reducing alkaline medium, it being possible for these compositions to be used for dyeing keratin fibres and in particular human hair.

The use of oxidation dyestuff precursors is widespread in the field of hair colouration. This class of dyestuffs includes compounds which are initially weakly coloured or colourless and are commonly referred to as "oxidation bases", and which develop their tinctorial strength in the hair, in the presence of oxidising agents, leading to the formation of coloured compounds. The formation of these coloured compounds results either from oxidative condensation of the "oxidation bases" with themselves, or from oxidative condensation of the "oxidation bases" with compounds commonly referred to as "couplers", which are generally present in the dyeing compositions used in oxidation dyeing.

The variety of the molecules used, which consist on the one hand of the "oxidation bases" and on the other hand of the "couplers", makes it possible to obtain a very rich range of colours in terms of the natural or ashen tints, which cannot easily be obtained by other means.

In general, these tints also possess excellent properties for masking white hair. Furthermore, they are generally fairly fast to external agents such as light and washing.

On the other hand, in terms of the sheen of the colours, if it is desired to obtain warm shades such as golden, copper, mahogany and red shades, satisfactory "oxidation base"/"coupler" combinations are rare. In particular, they frequently have a low fastness to light, which very frequently causes the shade on the hair to change with time, with a loss of sheen. Furthermore, in this type of shade, combinations of oxidation dyestuff precursors are frequently criticised for their lack of luminosity.

To overcome these two disadvantages, it is well known to use direct dyestuffs, that is to say coloured substances imparting a colouration in the absence of an oxidising agent, in combination with oxidation dyestuff precursors.

These direct dyestuffs are generally either yellow dyestuffs, or orange dyestuffs, or red dyestuffs, depending on the desired dyeing effect. To obtain the desired sheen, it is of course possible to use a mixture of these various dyestuffs.

As the direct dyestuffs are by definition auxiliary dyestuffs when they are used in oxidation dyes, they must be able to withstand the oxidative process which enables the oxidation dyestuff precursors to develop their colouration. This requirement considerably reduces the range of direct dyestuffs which can be used in oxidation dyeing.

It has been shown that, amongst the direct dyestuffs which can be used, the nitro dyestuffs of the benzene series appear to be best suited to the requirements of the formulator, essentially because of the richness and the luminosity of their colours.

The use of such dyestuffs in combination with the oxidation dyestuff precursors has formed the subject of numerous patents.

These direct dyestuffs include, in particular, nitro-para-phenylenediamine, which gives red shades which are greatly valued by the formulator for producing tints with copper, mahogany and red sheens.

It is also known to use certain red or purple-red dyestuffs and in particular 5-N-($\beta$-hydroxyethyl)-amino-4-chloro-2-amino-nitrobenzene (U.S. Pat. No. 3,973,900). Unfortunately, the use of these nitro dyestuffs of the benzene series is limited because of two disadvantages.

Firstly, as the oxidation dyestuff precursors are by definition sensitive to oxidising agents and in particular to oxidation by air, a reducing agent must be added to the oxidation dyeing compositions to prevent the premature oxidation of these precursors before the moment chosen for developing the colouration on the hair, for example during storage.

The most widely used reducing agents, in particular sodium bisulphite, are particularly reactive towards numerous nitro dyestuffs of the benzene series, and this reactivity is further enhanced by the generally alkaline character of the oxidation dyeing compositions. This reactivity of the reducing agent results in a gradual loss of the tinctorial strength of the nitro dyestuffs of the benzene series during storage of the dyeing compositions before they are used.

Secondly, the work of Doctor Ames has demonstrated that certain nitro derivatives of the benzene series, in particular nitro-para-phenylenediamine, possess a potential mutagenic power, which discourages the use of these dyestuffs in hair-dyeing compositions.

We have now discovered that, surprisingly, certain nitro derivatives of the benzene series possess the dual characteristic of being stable in the presence of conventional reducing agents such as, for example, sodium bisulphite, in alkaline compositions for oxidation dyeing, and of being non-mutagenic on the various strains of salmonella.

It will be recalled that the non-mutagenic character of dyestuffs is assessed using the Ames test on Salmonella typhimurium, with or without S9 mix, non-activated or activated by Arochlor 1254, and this is carried out on the five strains TA 1535, TA 1537, TA 100, TA 1538 and TA 98.

As regards the Ames test, reference may be made to the following literature:

B. N. Ames, H. O. KAMMEN and E. YAMASAKI, "Dyes are mutagenic; Identification of a variety of mutagenic ingredients", Proc. Nat. Acad. Sci. USA, Volume 72, No. 6, pages 2,423–2,427 (June 1975); and B. N. Ames, J. Mc CANN and E. YAMASAKI, "Methods for detecting carcinogens and mutagens with Salmonella mammalian microsome mutagenicity test", Mutation Res., 31 (1975), pages 347–364.

We have also discovered that certain combinations of non-mutagenic dyestuffs, including the nitro dyestuffs of the benzene series used according to the invention, one of which is a red dyestuff, make it possible to replace the nitro-para-phenylenediamine to obtain the sheens provided by this dyestuff.

The nitro dyestuffs of the benzene series possessing the dual characteristic indicated above and selected for their tinctorial strength, which can be used according to the invention, have the following general formula:

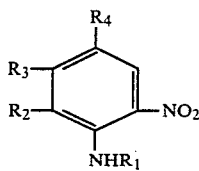 (I)

in which $R_1$ denotes a methyl group, $R_2$ and $R_4$ denote hydrogen and $R_3$ denotes the β-hydroxyethoxy group, or alternatively $R_1$, $R_3$ and $R_4$ denote hydrogen and $R_2$ denotes a methyl or hydroxyl group, or alternatively $R_1$ and $R_2$ denote hydrogen, $R_3$ denotes a methyl group and $R_4$ denotes a hydroxyl, N-(β-hydroxyethyl)-amino or (β-N,N-diethylaminoethyl)-amino group, or $R_1$, $R_2$ and $R_3$ denote hydrogen and $R_4$ denotes the N,N-bis-(β-hydroxyethyl)-amino group.

These nitro dyestuffs of the benzene series are particularly valuable because they make it possible to obtain a wide range of colours when they are used in oxidation dyeing compositions. In fact, when they are used in oxidation dyeing compositions, these dyestuffs give colours ranging from yellow-green to yellow, to orange and to red.

Furthermore, the shades obtained with oxidation dyeing compositions containing these dyestuffs are stable to light, which makes it possible substantially to prevent the changing and weakening of the shades on hair exposed to the sun.

The present invention accordingly provides a dyeing composition for dyeing keratin fibres and in particular human hair, in a reducing alkaline medium, which comprises at least one oxidation dyestuff precursor in combination with at least one direct dyestuff, in an aqueous vehicle, the direct dyestuff or dyestuffs being nitro derivatives of the benzene series of formula (I) as defined above.

The present invention also provides a process for dyeing keratin fibres and in particular human hair, using the dyeing compositions of this invention.

A more particularly preferred combination of nitro direct dyestuffs of the benzene series is that which contains 5-N-(β-hydroxyethyl)-amino-4-methyl-2-amino-nitrobenzene, which is a red dyestuff, in combination with 3-hydroxy-2-amino-nitrobenzene or 5-hydroxy-4-methyl-2-amino-nitrobenzene.

This preferred combination makes it possible, in particular, to replace the nitro-para-phenylenediamine to obtain the sheens provided by this dyestuff, and has the advantage of being stable in a reducing alkaline medium, which is not the case with the 5-N-(β-hydroxyethyl)-amino-4-chloro-2-amino-nitrobenzene used in oxidation dyeing in U.S. Pat. No. 3,973,900.

The nitro dyestuffs of the benzene series used according to the invention are known compounds, with the exception of 5-N-(β-hydroxyethyl)-amino-4-methyl-2-aminonitrobenzene and 5-(β-N,N-diethylaminoethyl)-amino-4-methyl-2-amino-nitrobenzene, which are new compounds.

The preparation of these new compounds is described in the Examples below.

The nitro dyestuffs of the benzene series used in the present invention can be used in combination with all the oxidation dyestuff precursors normally used in oxidation dyes.

Amongst the oxidation dyestuff precursors which can be used in the dyeing compositions according to the invention, examples which may be mentioned include para-phenylenediamines in which one of the amine groups is primary, it being possible for the other to be primary, secondary or tertiary, and which are substituted or unsubstituted on the benzene nucleus, para-aminophenols with an optionally substituted, primary amine group, tetraaminopyrimidines in which the amine groups can be substituted or unsubstituted, meta-phenylenediamines substituted or unsubstituted on the amine groups and also on the benzene nucleus, polyphenols substituted or unsubstituted on the benzene nucleus, and in particular resorcinol and its derivatives, naphthols, and meta-aminophenols optionally substituted on the amine group and/or on the benzene ring.

The dyeing compositions according to the invention contain one or more nitro dyestuffs of the benzene series defined by the formula (I) above, and stable in an alkaline reducing medium, suitably in an amount from 0.005 to 3% and preferably 0.05 to 1.5% by weight, based on the total weight of the composition.

The oxidation dyestuff precursor or precursors are suitably present in the dyeing compositions according to the invention in an amount from 0.001 to 25% and preferably from 0.01 to 15% by weight, based on the total weight of the composition.

The reducing agents which can be used in the dyeing compositions according to the invention consist, in particular, of sodium bisulphite, but can also be, for example, thioglycolic acid, thiolactic acid and their salts, and the other compounds normally used as reducing agents in oxidation dyeing. These reducing agents are suitably used in an amount from 0.005 to 3% by weight and preferably 0.1 to 1.5% by weight, based on the total weight of the composition.

The dyeing compositions of the invention can also contain antioxidants, such as hydroquinone, generally in a concentration from 0.005 to 1% and preferably from 0.05 to 0.5% by weight, based on the total weight of the composition.

The dyeing compositions according to the invention can be presented in various forms, but the forms which are more particularly advantageous are creams, and liquids which give gels or creams on dilution.

For this purpose, the dyeing compositions according to the invention can contain anionic, cationic, non-ionic or amphoteric surface-active agents or mixtures thereof.

The surface-active agents are conveniently present in the compositions according to the invention in an amount from 0.5 to 55% by weight and preferably from 4 to 45% by weight, relative to the total weight of the composition.

Organic solvents can also be included in the compositions according to the invention in order to solubilise compounds which would not otherwise be sufficiently soluble in water. Suitable solvents include benzyl alcohol, phenylethyl alcohol, lower alkanols such as ethanol or isopropanol, polyols such as glycerol, glycols or glycol ethers, such as 2-butoxyethanol, ethylene glycol, ethylene glycol monoethyl ether, propylene glycol and diethylene glycol monoethyl ether and monomethyl ether. These solvents are preferably present in an amount from 1 to 75% by weight and more particularly from 5 to 50% by weight, relative to the total weight of the composition.

The compositions according to the invention can also contain one or more thickeners, dispersing agents, hair conditioners, compounds for sequestering metal ions, bactericides and perfumes, and also any other adjuvant normally used in cosmetics.

The pH of the dyeing compositions according to the invention is preferably alkaline and more particularly from 8 to 11.5. It can be adjusted to the desired value using an alkalising agent such as ammonia, ammonium, sodium or potassium carbonates, an alkanolamine such as mono-, di or tri-ethanolamine, sodium hydroxide or potassium hydroxide, or an alkylamine such as ethylamine or triethylamine or using an acidifying agent such as phosphoric, hydrochloric, tartaric, acetic, lactic or citric acid.

The dyeing compositions according to the invention can be applied as such to keratin fibres and in particular to hair. The colouration can then be developed slowly in the presence of the oxygen in the air, but it is preferred to use a chemical developing system, which is most frequently a solution of hydrogen peroxide, urea peroxide or a per-salt. A solution of hydrogen peroxide is preferably used.

The dyeing composition according to the invention is typically applied, as such or diluted with an oxidising agent, to dry or damp hair, left on the hair for, say, 3 to 60 minutes, preferably for 5 to 45 minutes, and the hair is then rinsed, optionally shampooed and rinsed again, and dried.

The following Examples further illustrate the present invention.

PREPARATION EXAMPLE 1

Preparation of 5-N-(β-hydroxyethyl)-amino-4-methyl-2-aminonitrobenzene.

The reaction scheme is as follows:

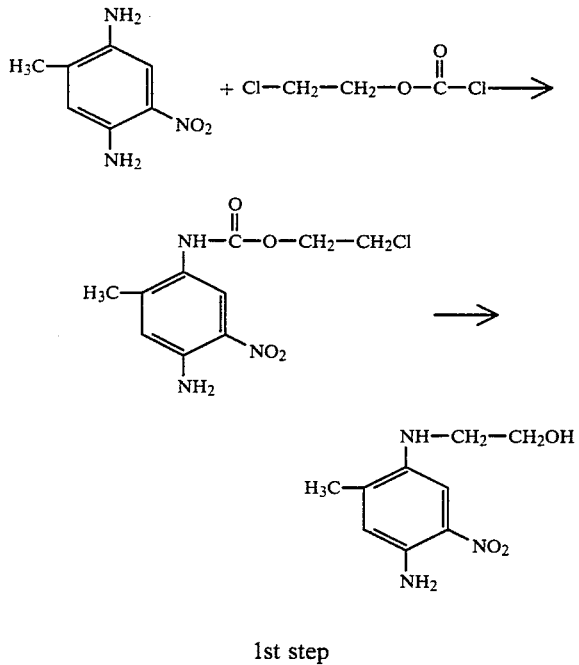

1st step

Preparation of β-chloroethyl N-(2-methyl-4-amino-5-nitrophenyl)-carbamate.

0.6 mol (100 g) of 4-methyl-2,5-diamino-nitrobenzene and 0.36 mol (50 g) of potassium carbonate are introduced into 500 ml of dioxane to which 145 ml of water have been added. The mixture is heated to 90° C., whilst stirring, and 0.6 mol (86 g) of chloroethyl chloroformate is then added gradually, in the course of 10 minutes. When the addition has ended, the heating is maintained for 10 minutes at 90° C. The reaction medium is cooled to 15° C. and the desired product is then filtered off. After washing with a small amount of dioxane and then with water and alcohol, the product is recrystallised from dioxane and then dried in vacuo. It melts at 192° C.

| Analysis | Calculated for $C_{10}H_{12}N_3O_4Cl$ | Found |
|---|---|---|
| C % | 43.87 | 43.85 |
| H % | 4.39 | 4.43 |
| N % | 15.35 | 15.25 |
| O % | 23.40 | 23.60 |
| Cl % | 12.98 | 12.78 |

2nd step

Preparation of 5-N-(β-hydroxyethyl)-amino-4-methyl-2-amino-nitrobenzene 1.86 mols (510 g) of β-chloroethyl N-(2-methyl-4-amino-5-nitrophenyl)-carbamate are introduced, at 55° C., in the course of 15 minutes, whilst stirring, into 2,625 ml of an aqueous-alcoholic solution (30% of $H_2O$, 70% of ethanol) containing 9.32 mols (522 g) of potassium hydroxide. The temperature rises to 72° C. When the addition has ended, one liter of water is added to the reaction medium, whilst keeping the reaction medium at between 70° and 75° C. The hot reaction medium is filtered to remove a small amount of insoluble material. 5 liters of iced water are added to the filtrate and the mixture is then neutralised with acetic acid. The desired product precipitates. It is filtered off, washed with water and recrystallised from alcohol. After drying in vacuo, it melts at 141° C.

| Analysis | Calculated for $C_9H_{13}N_3O_3$ | Found |
|---|---|---|
| C % | 51.18 | 51.13 |
| H % | 6.16 | 6.18 |
| N % | 19.91 | 19.86 |
| O % | 22.75 | 22.64 |

PREPARATION EXAMPLE 2

Preparation of 5-(β-N,N-diethylaminoethyl)-amino-4-methyl-2-aminonitrobenzene

The reaction scheme is as follows:

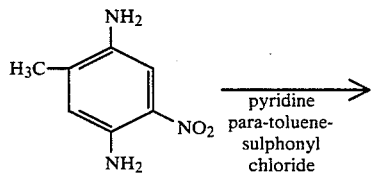

-continued

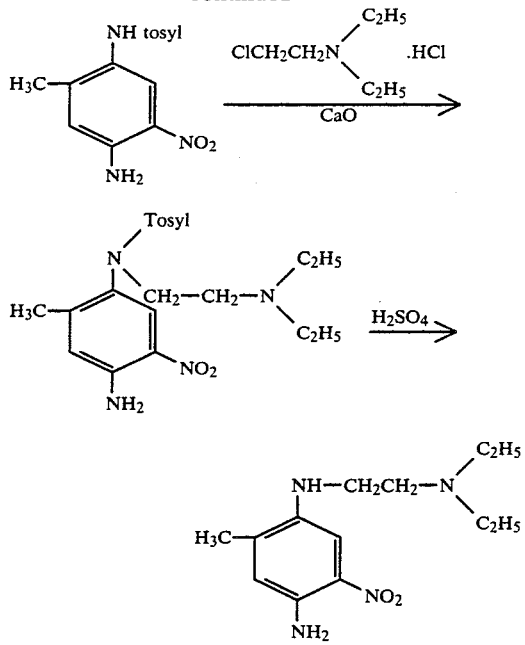

1st step

Preparation of
5-N-tosylamino-4-methyl-2-amino-nitrobenzene 0.149 mol (25 g) of 2-methyl-5-nitro-para-phenylenediamine is dissolved in 75 ml of pyridine. 0.161 mol (30.5 g) of para-toluenesulphonyl chloride is added gradually to this pyridine solution, at 40° C., whilst stirring, and the reaction medium is then kept at 40° C. for 4 hours. The pyridine solution is then poured into 600 g of iced water.

The desired product precipitates on adding hydrochloric acid. It is filtered off, washed with water and then recrystallised from acetic acid. After drying in vacuo, it melts at 174° C.

| Analysis | Calculated for $C_{14}H_{15}H_3O_4S$ | Found |
|---|---|---|
| C % | 52.34 | 52.47 |
| H % | 4.67 | 4.70 |
| N % | 13.08 | 12.96 |
| O % | 19.94 | 20.05 |
| S % | 9.97 | 9.79–9.93 |

2nd step

Preparation of
5-N-(β-N',N'-diethylaminoethyl)-N-tosylamino-4-methyl-2-amino-nitrobenzene 0.02 mol (6.42 g) of 5-N-tosylamino-4-methyl-2-amino-nitrobenzene and 0.03 mol (1.68 g) of lime are introduced into 24 ml of dimethylformamide. The mixture is heated to 80° C. and 0.022 mol (3.8 g) of diethylaminoethyl chloride is then introduced gradually, whilst stirring. The temperature is kept at 80° C. for 1 hour 15 minutes and the reaction medium is then poured into 100 ml of iced water. The desired product precipitates. It is filtered off, washed with water and then recrystallised from dioxane. After drying in vacuo at 50° C., it melts at 181° C.

| Analysis | Calculated for $C_{20}H_{28}N_4O_4S$ | Found |
|---|---|---|
| C % | 57.14 | 57.21 |
| H % | 6.67 | 6.65 |
| N % | 13.33 | 13.28 |
| O % | 15.24 | 15.34 |
| S % | 7.82 | 7.50–7.67 |

3rd step

Preparation of
5-(β-N,N-diethylaminoethyl)-amino-4-methyl-2-amino-nitrobenzene 0.0426 mol (17.9 g) of the substituted paratoluenesulphonamide obtained in the preceding step is introduced gradually, whilst stirring, into 90 ml of sulphuric acid at 0° C. When the solid has dissolved, the reaction medium is kept at 0° C. for 3 hours and then poured onto 700 g of crushed ice. The mixture is neutralised with ammonia. The desired product, which has precipitated, is filtered off. After washing with water, drying and recrystallisation from ethyl acetate, it melts at 78° C.

| Analysis | Calculated for $C_{13}H_{22}N_4O_4$ | Found |
|---|---|---|
| C % | 58.65 | 58.50 |
| H % | 8.27 | 8.29 |
| N % | 21.05 | 21.15 |
| O % | 12.03 | 12.15 |

EXAMPLE 1

The following dyeing composition, which is in the form of a cream, is prepared:

| | |
|---|---|
| 1-N,N—Bis-(β-hydroxyethyl)-amino-4-aminobenzene dihydrochloride | 0.3 g |
| Resorcinol | 1 g |
| Meta-aminophenol | 0.7 g |
| α-Naphthol | 0.1 g |
| 3-Methyl-2-amino-nitrobenzene | 0.25 g |
| 50/50 mixture of cetyl alcohol and stearyl alcohol | 18 g |
| 2-Octyldodecanol | 3 g |
| Cetyl/stearyl alcohol oxyethyleneated with 15 mols of ethylene oxide | 3 g |
| Ammonium lauryl-sulphate containing 30% of active ingredient | 12 g |
| Polymer consisting of units of the formula: | 3 g |

$$\left[ \begin{array}{cc} CH_3 & Cl^{\ominus} \\ | & \\ N^{\oplus} - (CH_2)_3 - \\ | & \\ CH_3 & \end{array} \begin{array}{cc} CH_3 & Cl^{\ominus} \\ | & \\ N^{\oplus} - (CH_2)_6 \\ | & \\ CH_3 & \end{array} \right]$$

| | |
|---|---|
| which can be prepared as described in French Patents 2,270,846 and 2,333,012 | |
| 22° Be strength ammonia solution | 12 g |
| Ammonium thiolactate (containing 50% in equivalents of thiolactic acid) | 0.8 g |
| Water q.s.p | 100 g |

This cream is diluted with one and a half times its weight of hydrogen peroxide of 20 volumes strength.

The mixture obtained, which is of creamy consistency, is applied to a deep chestnut head of hair for 30 minutes. After rinsing and drying, the hair has a dull chestnut colouration.

The result is substantially identical whether the operation is carried out with a freshly prepared cream or with a cream which has been stored for several weeks.

The use of the 3-methyl-2-amino-nitrobenzene according to the invention makes it possible to avoid having an excessively blue shade after storage, which would be the case if the yellow nitro direct dyestuff were unstable in the reducing alkaline medium.

EXAMPLE 2

The following dyeing composition is prepared:

| | |
|---|---|
| Para-phenylenediamine | 0.25 g |
| Para-aminophenol | 0.1 g |
| Resorcinol | 0.2 g |
| Meta-aminophenol | 0.1 g |
| 3-Hydroxy-2-amino-nitrobenzene | 0.5 g |
| 4-(β-Hydroxyethoxy)-2-N—methylamino-nitrobenzene | 0.05 g |
| Nonylphenol polyoxyethyleneated with 9 mols of ethylene oxide | 3 g |
| Oleyl alcohol | 9 g |
| Oleic diethanolamide | 9 g |
| Hydrogenated tallow amide containing 50 mols of ethylene oxide | 2.5 g |
| Oleic acid | 18 g |
| Polymer consisting of units of the formula: | 3 g |

$$\left[ \begin{array}{cc} CH_3 \; Cl^\ominus & CH_3 \; Cl^\ominus \\ | & | \\ N^\oplus-(CH_2)_3-N^\oplus-(CH_2)_6 \\ | & | \\ CH_3 & CH_3 \end{array} \right],$$

| | |
|---|---|
| which can be prepared as described in French Patents 2,270,846 and 2,333,012 | |
| Ethyl alcohol | 9 g |
| Benzyl alcohol | 11 g |
| Ethylenediaminetetraacetic acid | 0.2 g |
| 22° Be strength ammonia solution | 12.9 g |
| Monoethanolamine | 6.5 g |
| Ammonium thiolactate (containing 50% in equivalents of thiolactic acid) | 0.8 g |
| 1-Phenyl-3-methylpyrazol-5-one | 0.15 g |
| Water q.s.p. | 100 g |

This composition, which is in the form of a liquid, gives a creamy gel on dilution with an equal weight of hydrogen peroxide of 20 volumes strength.

This gel is applied to a deep blond head of hair for 30 minutes. The hair is rinsed and shampooed. A colouration in a golden light blond shade is obtained.

This golden sheen persists even if the dyeing composition used has been stored for several weeks to several months after manufacture.

EXAMPLE 3

The following dyeing composition is prepared:

| | |
|---|---|
| 2-Isopropyl-1,4-diaminobenzene dihydrochloride | 4.46 g |
| Para-aminophenol | 0.35 g |
| 2,4-Diaminophenoxy-ethanol dihydrochloride | 0.07 g |
| Resorcinol | 1.2 g |
| Meta-aminophenol | 0.5 g |
| 5-Hydroxy-4-methyl-2-amino-nitrobenzene | 0.4 g |
| Oleyl alcohol glycerolated with 2 mols of glycerol | 5 g |
| Oleyl alcohol glycerolated with 4 mols of glycerol | 5 g |
| Oleic acid | 5 g |
| Oleyldiethanolamine | 5 g |
| Oleic diethanolamide | 12 g |
| Ethyl alcohol | 10 g |
| Ethylglycol | 12 g |
| Ethylenediaminetetraacetic acid | 0.2 g |
| 22° Be strength ammonia solution | 12.4 g |
| 35° Be strength sodium bisulphite solution | 1.3 g |
| Hydroquinone | 0.15 g |
| 1-Phenyl-3-methylpyrazol-5-one | 0.15 g |
| Water q.s.p. | 100 g |

This liquid dyeing composition is mixed with an equal weight of hydrogen peroxide of 20 volumes strength.

This gives a gel which, when applied to deep chestnut hair for 30 minutes, imparts to the hair, after rinsing and shampooing, a coppery golden chestnut shade, and this is the case whether the operation is carried out starting with a freshly prepared liquid dyeing composition or with a liquid dyeing composition which has been stored for a long time before use.

EXAMPLE 4

The following dyeing composition is prepared:

| | |
|---|---|
| 2,3-Dimethyl-1,2-diaminobenzene dihydrochloride | 2 g |
| 2,4-Diaminophenoxy-ethanol dihydrochloride | 0.05 g |
| Resorcinol | 1.2 g |
| 2-Methylresorcinol | 0.2 g |
| 3-N—(β-Hydroxyethyl)-amino-6-methylphenol | 0.05 g |
| 5-N—(β-Hydroxyethyl)-amino-4-methyl-2-amino-nitrobenzene | 0.25 g |
| 3-Hydroxy-2-amino-nitrobenzene | 0.2 g |
| 50/50 mixture of cetyl alcohol and stearyl alcohol | 18 g |
| 2-Octyldodecanol | 3 g |
| Cetyl/stearyl alcohol oxyethyleneated with 15 mols of ethylene oxide | 3 g |
| Ammonium lauryl-sulphate containing 30% of active ingredient | 12 g |
| Polymer consisting of units of the formula: | 3 g |

$$\left[ \begin{array}{cc} CH_3 \; Cl^\ominus & CH_3 \; Cl^\ominus \\ | & | \\ N^\oplus-(CH_2)_3-N^\oplus-(CH_2)_6 \\ | & | \\ CH_3 & CH_3 \end{array} \right],$$

| | |
|---|---|
| which can be prepared as described in French Patents 2,270,846 and 2,333,012 | |
| 22° Be strength ammonia solution | 12 g |
| 35° Be strength sodium bisulphite solution | 1.5 g |
| Water q.s.p. | 100 g |

This dyeing composition is a cream which is mixed with 1.5 times its weight of hydrogen peroxide of 20 volumes strength.

The creamy mixture obtained is applied to a deep chestnut head of hair for 30 minutes. After rinsing and shampooing, an iridescent mahogany light chestnut shade is obtained.

This result remains unchanged whether the operation is carried out with a freshly prepared cream or with a cream which has been stored for several weeks. In particular, the iridescent mahogany sheen remains.

EXAMPLE 5

The following mixture is prepared:

| | |
|---|---|
| 2,6-Dimethyl-1,4-diaminobenzene dihydrochloride | 0.3 g |
| Para-aminophenol | 0.2 g |
| Resorcinol | 0.2 g |

-continued

| | |
|---|---|
| Meta-aminophenol | 0.1 g |
| Oleyl alcohol glycerolated with 2 mols of glycerol | 5 g |
| Oleyl alcohol glycerolated with 4 mols of glycerol | 5 g |
| Oleic acid | 5 g |
| Oleyldiethanolamine | 5 g |
| Oleic diethanolamide | 12 g |
| Ethyl alcohol | 10 g |
| Ethylglycol | 12 g |
| Ethylenediaminetetraacetic acid | 0.2 g |
| 22° Be strength ammonia solution | 10.2 g |
| 35° Be strength sodium bisulphite solution | 1.3 g |
| Hydroquinone | 0.15 g |
| 1-Phenyl-3-methylpyrazol-5-one | 0.15 g |
| Water q.s.p. | 100 g |

Three dyeing compositions A, B and C are prepared, which respectively contain the following compounds as nitro direct dyestuffs:

| | |
|---|---|
| A. Nitro-para-phenylenediamine | 0.15 g |
| B. 5-N—(β-Hydroxyethyl)-amino-4-methyl-2-amino-nitrobenzene | 0.25 g |
| 3-Hydroxy-2-amino-nitrobenzene | 0.2 g |
| C. 5-N—(β-Hydroxyethyl)-amino-4-chloro-2-amino-nitrobenzene | 0.29 g |
| 3-Hydroxy-2-amino-nitrobenzene | 0.16 g |

These three liquid compositions, mixed with an equal weight of hydrogen peroxide of 20 volumes strength, give a gel which is applied to deep blond hair for 30 minutes, and the hair is then rinsed. After shampooing and drying, a virtually identical, red iridescent light blond sheen is obtained in the three cases if the operation is carried out starting with freshly prepared liquid dyeing compositions.

In the opposite case, that is to say if the liquid dyeing compositions have been stored for a long period before use, it is found that only compositions A and B have a tinctorial strength which only changes slightly with time, whereas composition C gradually loses the red component of the sheen as a result of the instability of the 5-N-(β-hydroxyethyl)-amino-4-chloro-2-amino-nitrobenzene dyestuff in the presence of the sodium bisulphite in an alkaline medium, which instability is not found in the case of the 5-N-(β-hydroxyethyl)-amino-4-methyl-2-amino-nitrobenzene according to the invention.

EXAMPLE 6

The following mixture is prepared:

| | |
|---|---|
| 2,6-Dimethyl-1,4-diaminobenzene dihydrochloride | 0.3 g |
| Para-aminophenol | 0.2 g |
| Resorcinol | 0.2 g |
| Meta-aminophenol | 0.1 g |
| Oleyl alcohol glycerolated with 2 mols of glycerol | 5 g |
| Oleyl alcohol glycerolated with 4 mols of glycerol | 5 g |
| Oleic acid | 5 g |
| Oleyldiethanolamine | 5 g |
| Oleic diethanolamide | 12 g |
| Ethyl alcohol | 10 g |
| Ethylglycol | 12 g |
| Ethylenediaminetetraacetic acid | 0.2 g |
| 22° Be strength ammonia solution | 10.2 g |
| 35° Be strength sodium bisulphite solution | 1.3 g |
| Hydroquinone | 0.15 g |
| 1-Phenyl-3-methylpyrazolone | 0.15 g |

-continued

| | |
|---|---|
| Water q.s.p. | 100 g |

Three dyeing compositions D, E and F are prepared, which respectively contain the following compounds as dyestuffs:

| | |
|---|---|
| D. Nitro-para-phenylenediamine | 0.15 g |
| E. 5-N—(β-Hydroxyethyl)-amino-4-methyl-2-amino-nitrobenzene | 0.27 g |
| 5-Hydroxy-4-methyl-2-amino-nitrobenzene | 0.11 g |
| F. 5-N—(β-Hydroxyethyl)-amino-4-chloro-2-amino-nitrobenzene | 0.27 g |
| 5-Hydroxy-4-methyl-2-amino-nitrobenzene | 0.08 g |

These three liquid dyeing compositions give a gel when mixed with an equal weight of hydrogen peroxide of 20 volumes strength.

This gel is applied to a deep blond head of hair for 30 minutes. After rinsing and shampooing, the hair has a red iridescent light blond colouration, whichever of the three compositions D, E or F is used, if the operation is carried out starting with freshly prepared liquid compositions.

In the opposite case, if the compositions used have been stored for a long period before use, it is found that the sheen remains virtually unchanged with time in the case of compositions D and E, whereas the red component of the sheen gradually disappears in the case of composition F containing 5-N-(β-hydroxyethyl)-amino-4-chloro-2-aminonitrobenzene, which is unstable in the presence of the sodium bisulphite in an alkaline medium.

EXAMPLE 7

The following dyeing composition is prepared:

| | |
|---|---|
| 2,6-Dimethyl-1,4-diaminobenzene dihydrochloride | 0.07 g |
| Resorcinol | 0.1 g |
| 5-Hydroxy-4-methyl-2-amino-nitrobenzene | 0.1 g |
| 5-N—(β-Diethylaminoethyl)-amino-4-methyl-2-amino-nitrobenzene | 0.35 g |
| Nonylphenol polyoxyethyleneated with 9 mols of ethylene oxide | 3 g |
| Oleyl alcohol | 9 g |
| Oleic diethanolamide | 9 g |
| Hydrogenated tallow amide containing 50 mols of ethylene oxide | 2.5 g |
| Oleic acid | 18 g |
| Polymer consisting of units of the formula: | 3 g |

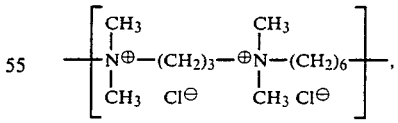

which can be prepared as described in French Patents 2,270,846 and 2,333,012

| | |
|---|---|
| Ethyl alcohol | 9 g |
| Benzyl alcohol | 11 g |
| Ethylenediaminetetraacetic acid | 0.2 g |
| 22° Be strength ammonia solution | 12.9 g |
| Monoethanolamine | 6.5 g |
| Ammonium thiolactate (containing 50% in equivalents of thiolactic acid) | 0.8 g |
| 1-Phenyl-3-methylpyrazol-5-one | 0.15 g |
| Water q.s.p | 100 g |

13

An equal weight of hydrogen peroxide of 20 volumes strength is added at the time of use and the composition is applied to deep blond hair. After an interval of 30 minutes, rinsing and washing, the hair has a light blond colouration with a golden iridescent sheen.

The shade remains unchanged if the composition used has been stored for a long period before use.

EXAMPLE 8

The following dyeing composition is prepared:

| | |
|---|---|
| Oleyl alcohol glycerolated with 2 mols of glycerol | 5 g |
| Oleyl alcohol glycerolated with 4 mols of glycerol | 5 g |
| Oleic acid | 5 g |
| Oleyldiethanolamine | 5 g |
| Oleic diethanolamide | 12 g |
| Ethyl alcohol | 10 g |
| Ethylglycol | 12 g |
| Ethylenediaminetetraacetic acid | 0.2 g |
| 22° Be strength ammonia solution | 10.2 g |
| 35° Be strength sodium bisulphite solution | 1.3 g |
| Hydroquinone | 0.15 g |
| 2,6-Dimethyl-1,4-diaminobenzene dihydrochloride | 0.6 g |
| Para-aminophenol | 0.3 g |
| Resorcinol | 0.65 g |
| Meta-aminophenol | 0.3 g |
| 2-Amino-5-N,N—bis-($\beta$-hydroxyethyl)-amino-nitrobenzene | 0.3 g |
| Water q.s.p. | 100 g |

An equal weight of hydrogen peroxide of 20 volumes strength is added at the time of use.

After leaving the composition for 30 minutes on a deep blond head of hair, rinsing and shampooing, the hair has a golden iridescent blond colouration and this is the case both with freshly prepared compositions and with compositions which have been stored for a long time before use.

We claim:

1. A composition suitable for dyeing human hair in a reducing alkaline medium which comprises 0.001 to 25% by weight of at least one oxidation base and at least one coupler as oxidation dyestuff precursors in combination with 0.005 to 3% by weight of at least one direct dyestuff, in an aqueous vehicle, said direct dyestuff being a nitro derivative of the formula:

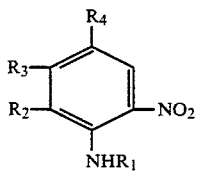

(I)

in which either (i) $R_1$ denotes methyl, $R_2$ and $R_4$ denote hydrogen and $R_3$ denotes $\beta$-hydroxyethoxy, or (ii) $R_1$, $R_3$ and $R_4$ denote hydrogen and $R_2$ denotes methyl or hydroxyl, or (iii) $R_1$ and $R_2$ denote hydrogen, $R_3$ denotes methyl and $R_4$ denotes hydroxyl, ($\beta$-hydroxyethyl)-amino or ($\beta$-N,N-diethylaminoethyl)-amino, or (iv) $R_1$, $R_2$ and $R_3$ denote hydrogen and $R_4$ denotes N,N-bis-($\beta$-hydroxyethyl)-amino.

2. A composition according to claim 1 wherein said at least one direct dyestuff comprises a combination of 5-N-($\beta$-hydroxyethyl)-amino-4-methyl-2-amino-nitrobenzene and 3-hydroxy-2-amino-nitrobenzene.

3. A composition according to claim 1 wherein said at least one direct dyestuff comprises a combination of 5-N-($\beta$-hydroxyethyl)-amino-4-methyl-2-amino-nitrobenzene and 5-hydroxy-4-methyl-2-amino-nitrobenzene.

4. A composition according to claim 1 which contains 0.05 to 1.50% by weight of at least one derivative of formula (I), based on the total weight of the composition.

5. A composition according to claim 1 which contains 0.01 to 15% by weight of oxidation dyestuff precursors, based on the total weight of the composition.

6. A composition according to claim 1 which contains at least one reducing agent in an amount of from 0.05 and 3% by weight, based on the total weight of the composition.

7. A composition according to claim 6 which contains 0.1 to 1.5% by weight of at least one reducing agent, based on the total weight of the composition.

8. A composition according to claim 6 or 7 in which the reducing agent is sodium bisulphite or thiolactic or thioglycolic acid or a salt thereof.

9. A composition according to claim 6 which contains an antioxidant in an amount from 0.005 to 1% by weight, based on the total weight of the composition.

10. A composition according to claim 9 which contains 0.05 to 0.5% by weight of antioxidant, based on the total weight of the composition.

11. A composition according to claim 1 which contains at least one surface-active agent, in an amount from 0.5 to 55% by weight, based on the total weight of the composition.

12. A composition according to claim 11 which contains 4 to 45% by weight of the surface-active agent, based on the total weight of the composition.

13. A composition according to claim 1 which contains organic solvent in an amount from 1 to 75% by weight, based on the total weight of the composition.

14. A composition according to claim 13 which contains 5 to 50% by weight of organic solvent, based on the total weight of the composition.

15. A composition according to claim 1 which contains at least one thickener, dispersing agent, hair conditioner, compound for sequestering the metal ions, or perfume.

16. A composition according to claim 1 which has a pH from 8 to 11.5.

17. Process for dyeing human hair which comprises applying thereto a composition as defined in claim 1, leaving it on the hair for 3 to 60 minutes and then rinsing, optionally shampooing and rinsing the hair again, and drying it.

18. A composition according to claim 1 wherein said direct dyestuff is 5-N-($\beta$-substituted ethyl)amino-4-methyl-2-amino-nitrobenzene wherein the $\beta$-substituent is hydroxy or diethylamino.

19. A composition according to claim 1 wherein said direct dyestuff is 5-N-($\beta$-hydroxyethyl)-amino-4-methyl-2-aminonitrobenzene.

20. A composition according to claim 1 wherein said at least one oxidation base is selected from the group consisting of paraphenylenediamines, paraaminophenols, and tetraaminopyrimidines and said at least one coupler is selected from the group consisting of metaphenylenediamines, polyphenols, naphthol and tetraaminopyrimidines.

21. A composition according to claim 1 wherein said direct dyestuff is 5-N-($\beta$-diethylaminoethyl)amino-4-methyl-2-amino-nitrobenzene.

* * * * *